US008966686B2

(12) United States Patent
Wiggers et al.

(10) Patent No.: US 8,966,686 B2
(45) Date of Patent: Mar. 3, 2015

(54) COUCH TOP PITCH AND ROLL MOTION BY LINEAR WEDGE KINEMATIC AND UNIVERSAL PIVOT

(75) Inventors: Robert T. Wiggers, Belmont, CA (US); Bernhard Pultar, Dietikon (AT); Daniel Seiler, Wettingen (CH); Pascal T. Hofer, Buchs (CH); Reto W. Filiberti, Steinhausen (CH); Christof Frey, Hunzenschwil (CH)

(73) Assignees: Varian Medical Systems, Inc., Palo Alto, CA (US); Varian Medical Systems International AG (CH)

( * ) Notice: Subject to any disclaimer, the term of this patent is extended or adjusted under 35 U.S.C. 154(b) by 446 days.

(21) Appl. No.: 13/290,525

(22) Filed: Nov. 7, 2011

(65) Prior Publication Data

US 2013/0111668 A1 May 9, 2013

(51) Int. Cl.
*A61G 13/00* (2006.01)
(52) U.S. Cl.
USPC .................................... 5/608; 5/607; 5/600
(58) Field of Classification Search
USPC .................................... 5/607–608, 610–611
See application file for complete search history.

(56) References Cited

U.S. PATENT DOCUMENTS

| 4,885,998 A | 12/1989 | Span et al. |
| 6,502,261 B1 | 1/2003 | Harwood |
| 6,640,363 B1 * | 11/2003 | Pattee et al. .......................... 5/601 |
| 6,865,411 B2 | 3/2005 | Erbel et al. |
| 2005/0228255 A1 | 10/2005 | Saracen et al. |
| 2007/0189461 A1 | 8/2007 | Sommer |
| 2007/0230660 A1 | 10/2007 | Herrmann |
| 2010/0222724 A1 * | 9/2010 | Huang .......................... 601/115 |

FOREIGN PATENT DOCUMENTS

FR 2765487 A1 7/1997

OTHER PUBLICATIONS

"To the Power of Six," HexaPOD™ RTC, Elekta Oncology, 8 pages.
"FreeDOM Image Guided Robotic Patient Positioning System," Medical Intelligence, HexaPOD™ RTC, 4 pages.
"Protura Robotic Patient Positioning," CIVCO Medical Solutions, 4 pages.
"Halcyon," Radiation Oncolocy, Fluke Biomedical, 15 pages.
"RT Robotic Patient Alignment," Novalis, 2 pages.
"Stewart platform," Wikipedia, 3 pages.

* cited by examiner

*Primary Examiner* — Fredrick Conley
(74) *Attorney, Agent, or Firm* — Patent Law Group LLP; David C. Hsia

(57) ABSTRACT

A couch top includes a top, a base, a universal joint coupling the top and the base, and actuators mounted on the base to pitch and roll the top. Feedback devices may be fitted on the rotating ends of the universal joint to provide feedback for a control loop. Each actuator has an actuated end that translates vertically to lift or lower the top. The vertical movement may be derived from a carriage riding in place on a translating inclined plane. When the actuated ends move in the same direction, they pitch the top. When the actuated ends move in the opposite directions, they roll the top. Feedback devices may be fitted on motors in the actuators to provide feedback for the control loop.

23 Claims, 12 Drawing Sheets

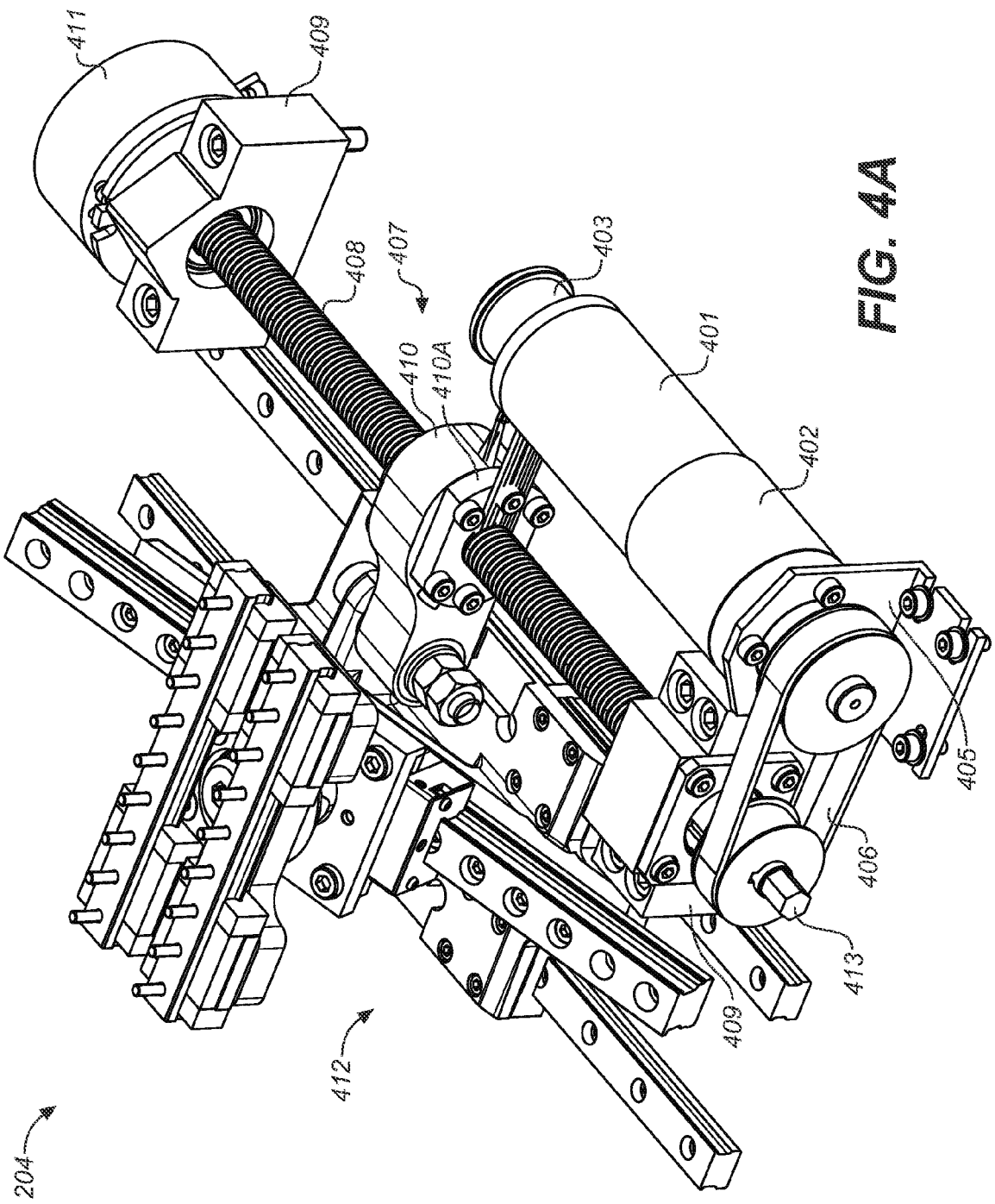

COUCH TOP PITCH AND ROLL MOTION BY LINEAR WEDGE KINEMATIC AND UNIVERSAL PIVOT

FIELD OF INVENTION

This invention relates to a patient positioning system, such as a couch, for radiotherapy treatment or simulation.

DESCRIPTION OF RELATED ART

Radiotherapy, also known as radiation oncology, is the medical use of ionizing radiation to destroy cancer cells in a malignant tumor. The goal of radiotherapy is to destroy as many cancer cells as possible while limiting harm to surrounding healthy tissue. A gantry or similar device is used to position a radiation delivery apparatus around the patient during radiation therapy. The patient can be positioned by an automatic couch with multiple degrees of freedom. The combination of gantry and couch movements provides greater flexibility in delivering the ionizing radiation to the patient.

SUMMARY

In one or more embodiments of the present disclosure, a couch top includes a top, a base, a universal joint coupling the top and the base, and actuators mounted on the base to pitch and roll the top. Feedback devices may be fitted on the rotating ends of the universal joint to provide feedback for a control loop. Each actuator has an actuated end that translates vertically to lift or lower the top. The vertical movement may be derived from a carriage riding in place on a translating inclined plane. When the actuated ends move in the same direction, they pitch the top. When the actuated ends move in the opposite directions, they roll the top. Feedback devices may be fitted on motors in the actuators to provide feedback for the control loop.

BRIEF DESCRIPTION OF THE DRAWINGS

In the drawings:

FIG. 4A shows an isometric assembled view of a wedge actuator in the couch top of FIG. 1 in one or more embodiments of the present disclosure;

Use of the same reference numbers in different figures indicates similar or identical elements.

DETAILED DESCRIPTION OF THE INVENTION

Figure 1:
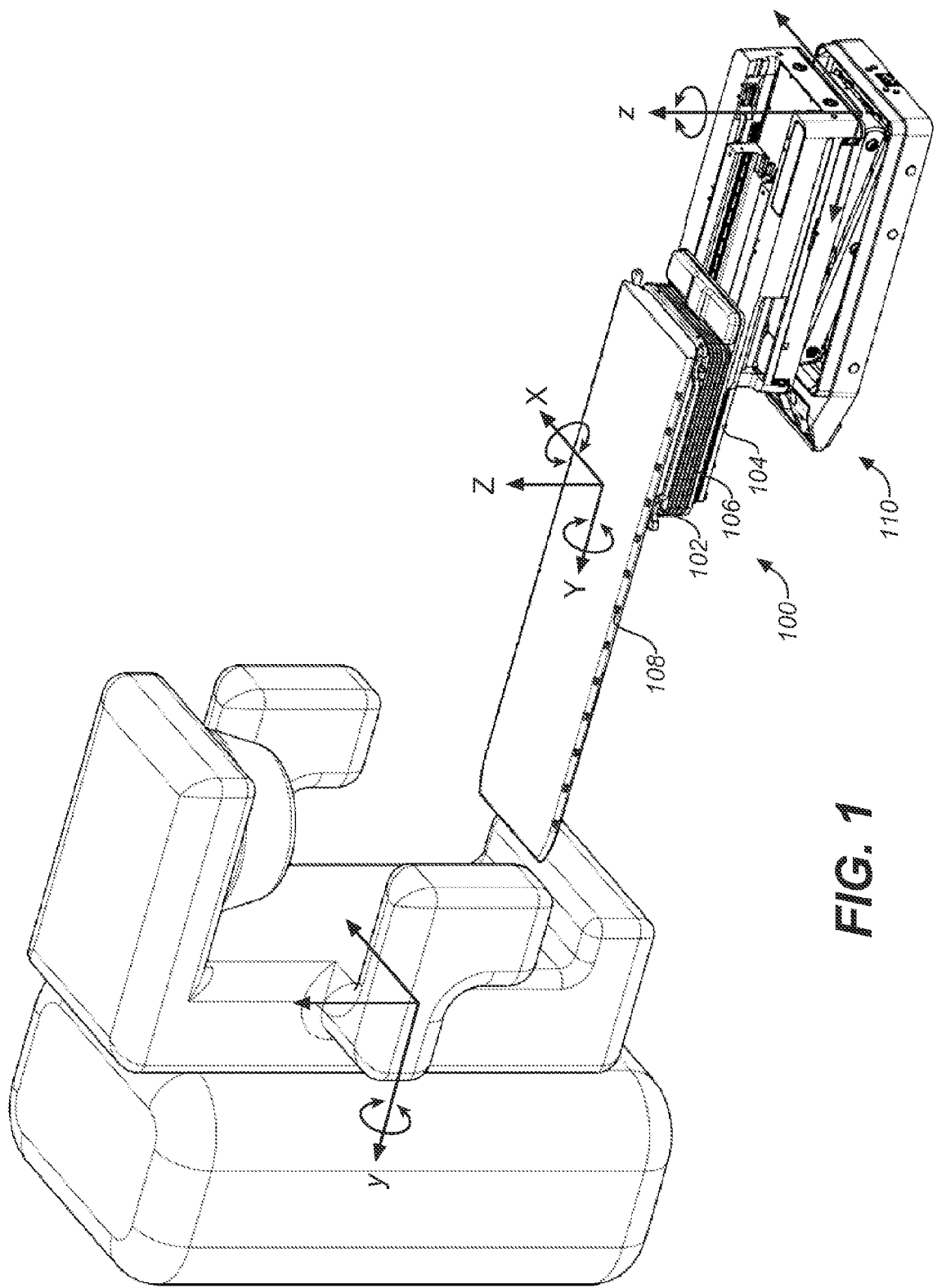
FIG. 1 shows an isometric view of a couch top with a bed and a treatment couch in one or more embodiments of the present disclosure.

FIG. 1 shows an isometric view of a couch top 100 in one or more embodiments of the present disclosure. Couch top 100 provides two degrees of freedom (2 DOF), such as pitch about an X-axis and roll about a Y-axis of a local coordinate system. X and Y-axes may be aligned with the physical axes of rotation of couch top 100, or X and Y-axes may be located away from the physical axes at or near a point where treatment is applied. Couch top 100 includes two main structural elements where one may be rotatable about X and Y-axes relative to the other. In one or more embodiments, couch top 100 includes a top 102 manipulated by actuating mechanisms mounted on a base 104 that is stationary relative to top 102. Alternatively the actuating mechanisms may be mounted to top 102. Top 102 and base 104 may each take the form of a plate, a frame, or another suitable shape. The actuating mechanisms may be protected and hidden from view by a bellow 106 between top plate 102 and base plate 104. A bed 108 for supporting a patient may be fixed to top plate 102. In one or more embodiments, base plate 104 may be mounted to a treatment couch 110 that provides four degrees of freedom (4 DOF), such as yaw about a Z direction and translation along X, Y, and Z directions. Note the use of "direction" means parallel to but not necessarily coincident with an axis. Together couch top 100 and treatment couch 110 make up a patient positioning system that provides six degrees of freedom (6 DOF).

Figure 2A:
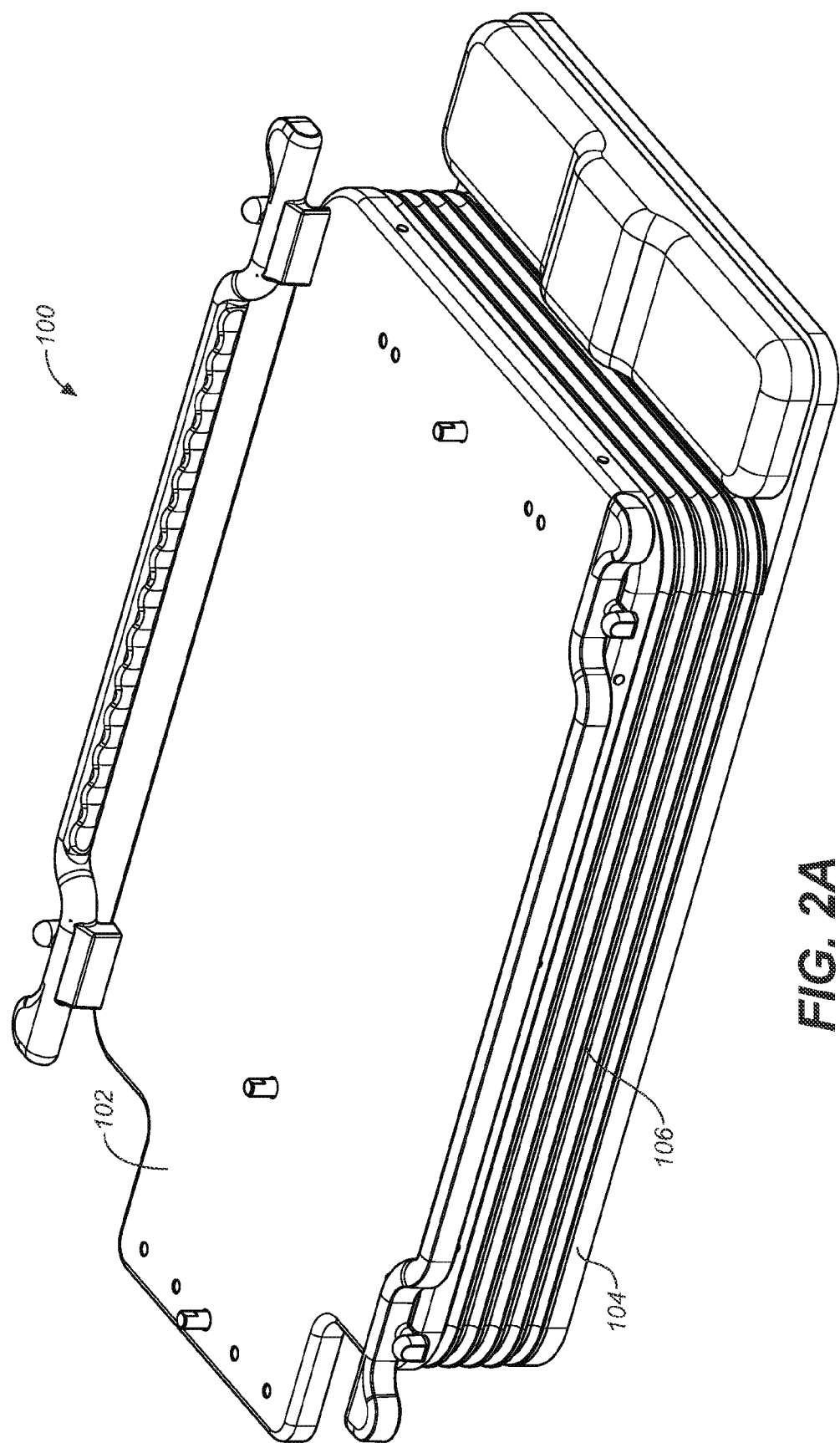
FIG. 2A shows an isometric view of the couch top of FIG. 1 in one or more embodiments of the present disclosure.
Figure 2B:
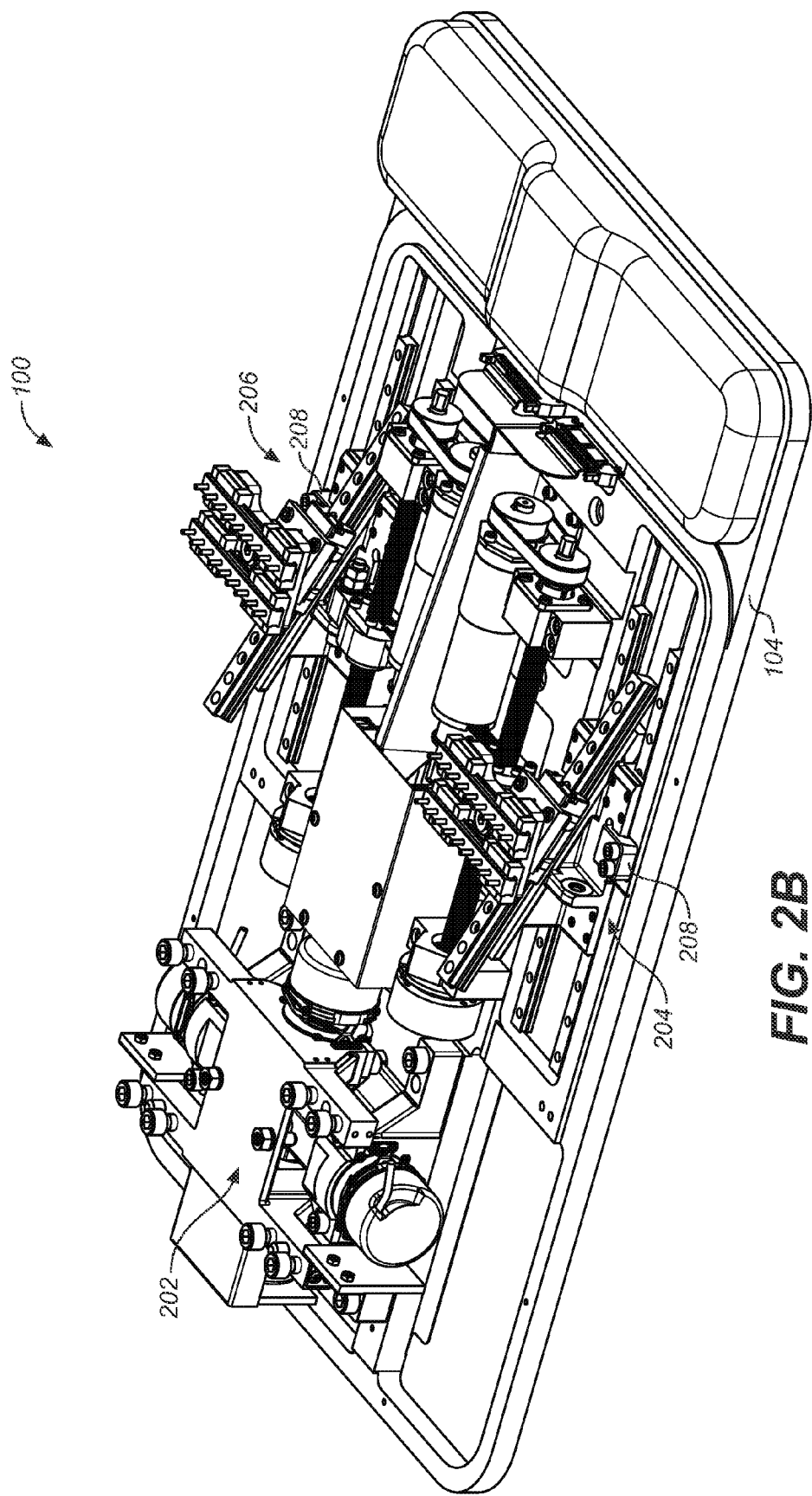
FIG. 2B shows an isometric view of the couch top of FIG. 1 without a top plate in one or more embodiments of the present disclosure.

FIG. 2A shows an isometric view of couch top 100 in one or more embodiments of the present disclosure. FIG. 2B shows an isometric view of couch top 100 without top plate 102 in one or more embodiments of the present disclosure. A universal joint 202 may be located at the forward end of couch top 100 toward a radiation delivery apparatus. Universal joint 202 may be mounted on base plate 104 and connected to the bottom of top plate 102 (FIG. 2A). Universal joint 202 acts as a fixed pivot point for top plate 102 to pitch about the X-axis and roll about the Y-axis. As alluded to above, the mechanical axes of universal joint 202 may be aligned to the X and the Y-axes of the local coordinate system. In practice, as long as the physical relationship between two coordinate systems is known, a controller can rotate top plate 102 about any given point in space with a given offset to the mechanical axes of couch top 100. The various coordinate systems include the coordinate systems local to couch top 100, treatment couch 110, and the radiation delivery apparatus. Rotary feedback devices may be directly connected to the shafts of universal joint 202 to detect the pitch and the roll angles. Rotary feedback devices may be absolute encoders, incremental encoders, resolvers, potentiometers, or a series of Hall-effect sensors. Details of an exemplary universal joint 202 are described later in reference to FIGS. 3A and 3B.

Top plate 102 (FIG. 2A) may be actuated by two identical, symmetrically arranged wedge actuators 204 and 206 mounted on base plate 104. Actuators 204 and 206 may be located near the back end of couch top 100 away from the radiation delivery apparatus. Alternatively, actuators 204 and 206 may be located at the forward end of couch top 100 toward the radiation delivery apparatus while universal joint 202 may be located at the back end of the couch top away from the radiation delivery apparatus. Wedge actuators 204 and 206 have actuated ends that provide two points of vertical support, on opposite sides of the Y-axis, to top plate 102. Near the middle of their travel, wedge actuators 204 and 206 hold top plate 102 substantially level. Each wedge actuator affects both pitches and rolls of top plate 102 at the same time due to the close mechanical coupling of top plate 102 and bottom plate 102 via universal joint 202 and actuators 204 and 206. However, actuators 204 and 206 may be controlled together or individually to provide independent pitch and roll motions as well as combined pitch and roll motions. For example, wedge actuators 204 and 206 vertically translate the vertical point supports in the same direction to pitch top plate 102 about the X-axis. Wedge actuators 204 and 206 vertically translate the vertical point supports in opposite directions to roll the top plate about the Y-axis. Any combination of pitch and roll motion is possible by setting the heights of the two points of wedge actuators 204 and 206. Details of exemplary wedge actuators 204 and 206 are described later in reference to FIG. 4. Brackets 208 from bottom plate 104 may lock wedge actuators 204 and 206 by fasteners to hold couch top 100 in a fixed orientation during transportation or in case of power or mechanical failure.

Figure 3A:
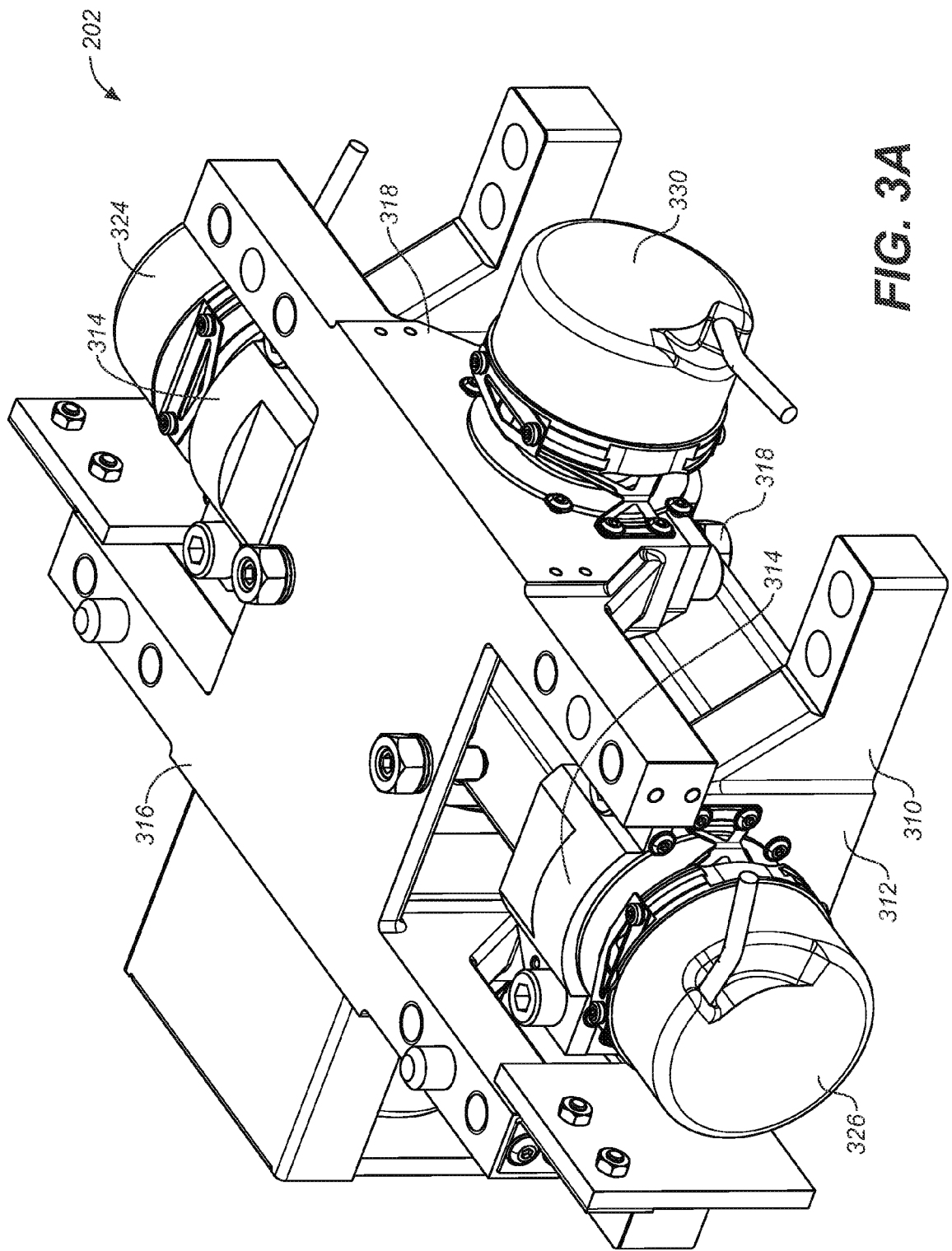
FIG. 3A shows an isometric assembled view of a universal joint in the couch top of FIG. 1 in one or more embodiments of the present disclosure.
Figure 3B:
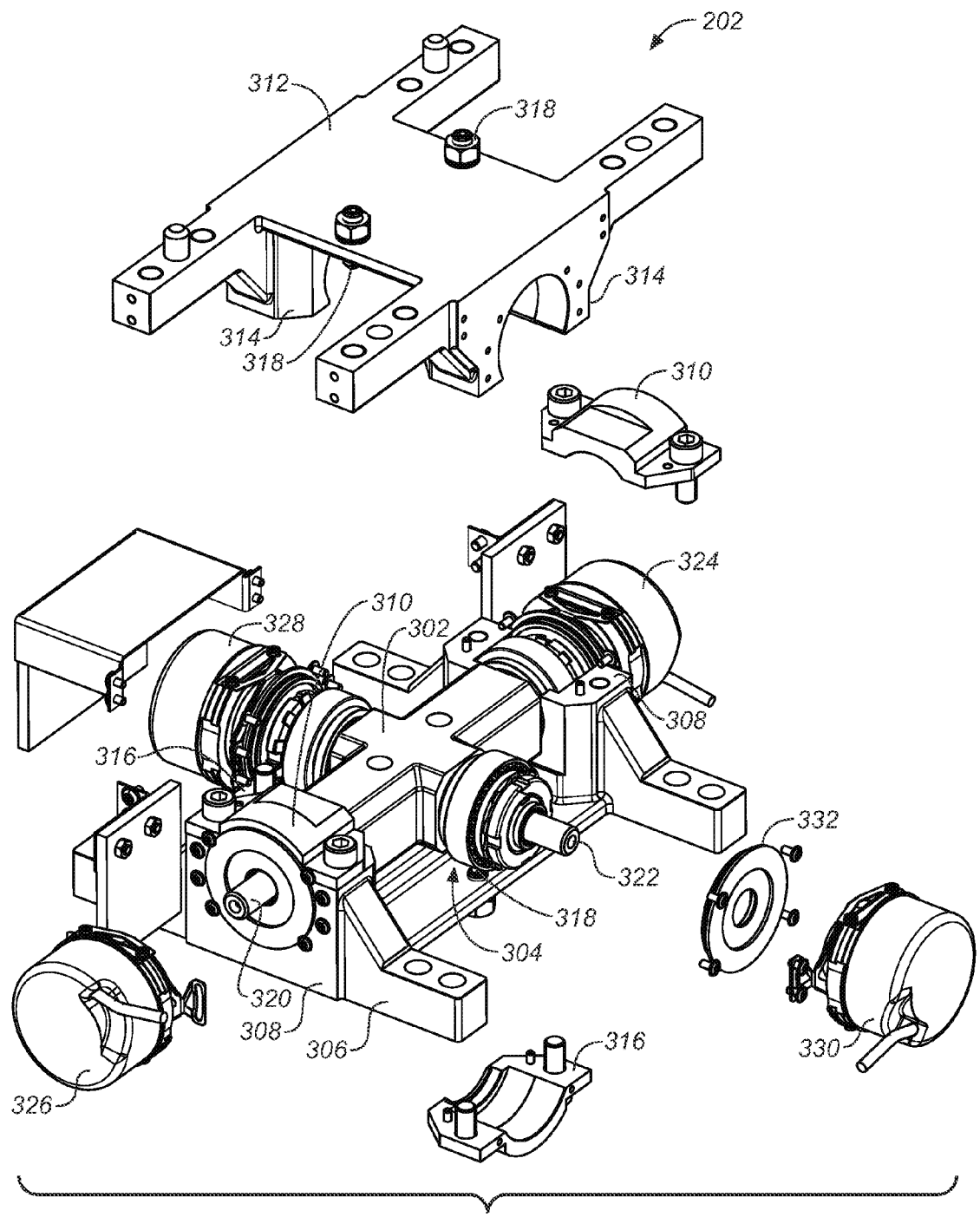
FIG. 3B shows a partially exploded view of the universal joint of FIG. 3A in one or more embodiments of the present disclosure.

FIG. 3A shows an isometric assembled view of universal joint 202 in one or more embodiments of the present disclosure. FIG. 3B shows a partially exploded view of universal joint 202 in one or more embodiments of the present disclosure. Universal joint 202 includes a cross shaft 302 with a pitch shaft and a roll shaft. The pitch and the roll shafts may be stepped to have segments of different diameters. Bearings 304 (only one is shown) fit over inner segments of the pitch and the roll shafts. Each bearing 304 may be an assembly of one or more bearings.

A lower mount 306 has two bearing housing bases 308 that receive bearings 304 on the pitch shaft. Bearing housing caps 310 may be secured to the open ends of bearing housing bases 308 to retain bearings 304. Lower mount 306 defines mounting holes for securing itself to base plate 104 (FIG. 2B). Lower mount 306 also defines mounting holes for receiving adjustable hardstops 318 (e.g., threaded nuts and bolts) that would hit the roll shaft to limit the total available pitch.

An upper mount 312 has two bearing housing bases 314 that receive bearings 304 on the roll shaft. Bearing housing caps 316 may be secured to the open ends of bearing housing bases 314 to retain bearings 304. Upper mount 312 defines mounting holes for securing itself to top plate 102 (FIG. 2A). Upper mount 312 also defines mounting holes for receiving adjustable hard stops 318 that would hit the pitch shaft to limit the total available roll.

End segments 320 and 322 of the pitch and the roll shafts protrude from bearings 304. In one or more embodiments, primary absolute encoder 324 and secondary absolute encoder 326 may be connected to the two end segments 320 of the pitch shaft to detect the absolute pitch angle of top plate 102 (FIG. 2A), and primary absolute encoder 328 and secondary absolute encoder 330 may be connected to the two end segments 322 of the roll shaft to detect the absolute roll angle of top plate 102. Both primary and the secondary encoders may be provided so their values can be compared to ensure they are functioning properly. Non-rotating reference component of each absolute encoder may be secured to the corresponding bearing housing. A hub 332 may be secured to the outward face of each bearing housing before the encoder to protect the bearing from debris. As discussed above, other rotary feedback devices may be used.

FIG. 4A shows an isometric assembled view of wedge actuator 204 in one or more embodiments of the present disclosure. Wedge actuator 206 (FIG. 2B) may be constructed in the same or similar manner.

Wedge actuator 204 includes a servo motor 401 that drives a planetary gear 402. A rotary feedback device may be mounted to servo motor 401 to measure the rotation of the motor shaft. The rotary feedback device may be a resolver, an absolute encoder, an incremental encoder, a potentiometer, or a Hall-effect sensor. In one or more embodiments, a resolver 403 may be mounted to servo motor 401. The motor assembly may be mounted by a bracket 405 to base plate 104 (FIG. 2B). Planetary gear 402 may be coupled by pulleys and a timing belt 406 to a screw drive 407 (e.g., a ball or lead screw drive). Screw drive 407 includes a spindle shaft 408 mounted by bearing housings 409 to base plate 104 along a first direction (e.g., the Y direction), a wedge link 410 containing or being attached to a ball screw or nut 410A fitted on the spindle shaft, and a brake 411 mounted to spindle shaft 408. Brakes may be applied to release or stop the rotation of spindle shaft 408 to provide precise motion control. Wedge link 410 may be connected to a wedge assembly 412 so they travel together when spindle shaft 408 rotates. Spindle shaft 408 has a patterned head 413 (e.g., a hex key) that accepts a hand crank to manually turn the spindle shaft in case of power or mechanical failure.

Figure 4B:
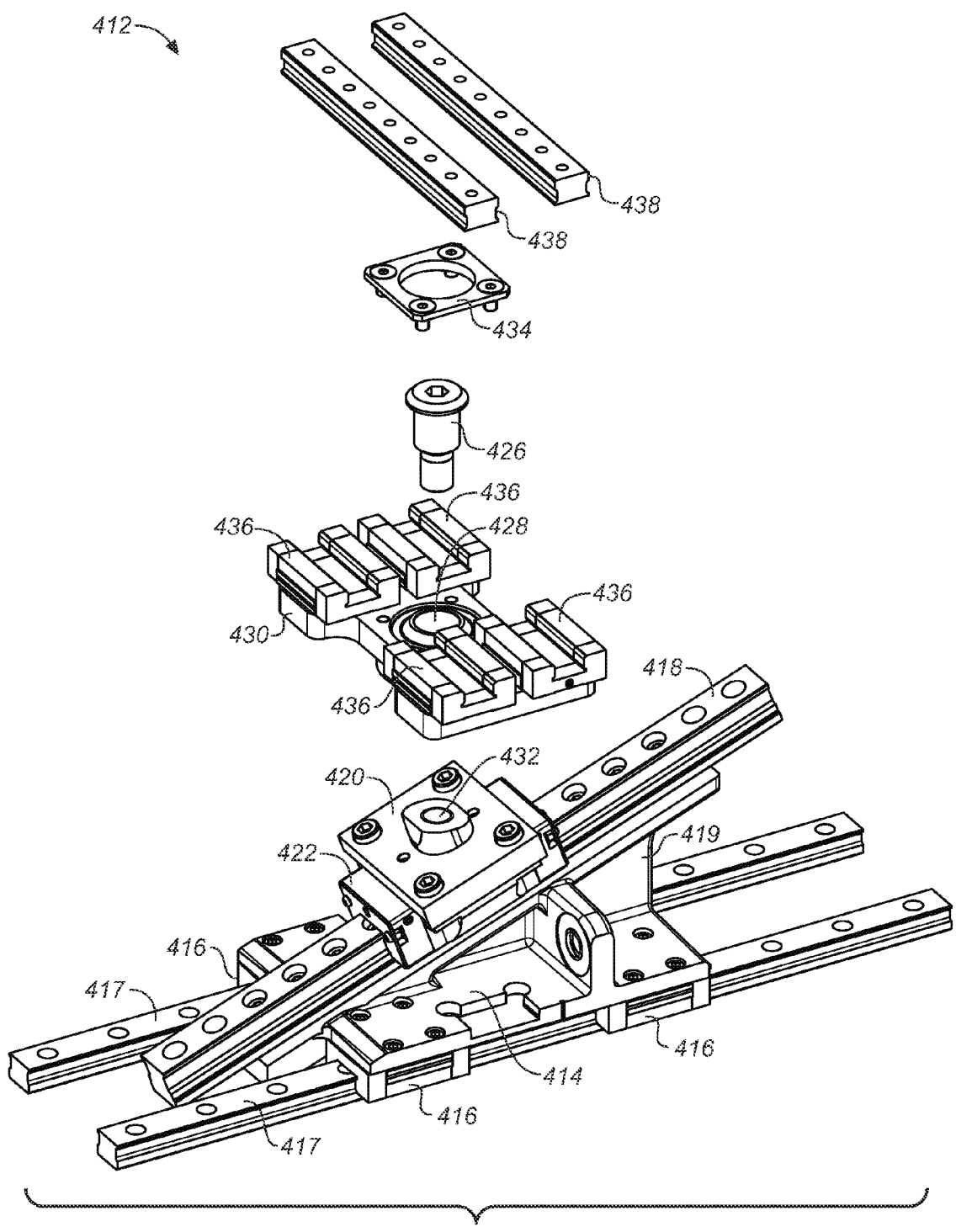
FIG. 4B shows a partially exploded view of a wedge assembly in the wedge actuator of FIG. 4A in one or more embodiments of the present disclosure.

FIG. 4B shows a partially exploded view of wedge assembly 412 in one or more embodiments of the present disclosure. Wedge assembly 412 includes a first carriage 414 with linear bearings 416 that ride on linear rails 417 mounted on base plate 104 (FIG. 2B) along the first direction (e.g., the Y direction). An inclined linear rail 418 may be mounted on an inclined plane 419 of first carriage 414. Inclined linear rail 418 may be aligned along the first direction (e.g., the Y direction) and inclined in the Z direction.

A second carriage 420 has linear bearing 422 that rides on inclined linear rail 418. A fastener 426 may be inserted through a spherical bushing 428 located in a platform 430, and secured to a threaded hole 432 on second carriage 420. A bushing cap 434 may be mounted to the top of platform 430 to retain spherical bushing 428. Linear bushings 436 may be mounted to the top of platform 430. Linear bushings 436 ride on linear rails 438 mounted to the bottom of top plate 102 (FIG. 2A) along a second direction (e.g., the X direction) orthogonal to the first direction.

As linear rails 438 is orthogonal to linear rails 417 and 418, linear rails 438 stop second carriage 420 from moving in the first direction (e.g., the Y direction) so the second carriage rides up and down in place on inclined linear rail 418 when first carriage 414 moves along the first direction. As second carriage 420 rides up and down on inclined linear rail 418, spherical bushing 428 provides a flexible coupling to accommodate for any pitch and roll motion of top plate 102 as fastener 426 may be limited to only vertical motion along the Z direction. Note that the top end of fastener 426 in spherical bushing 428 acts as a vertical support point to top plate 102.

Figure 5:
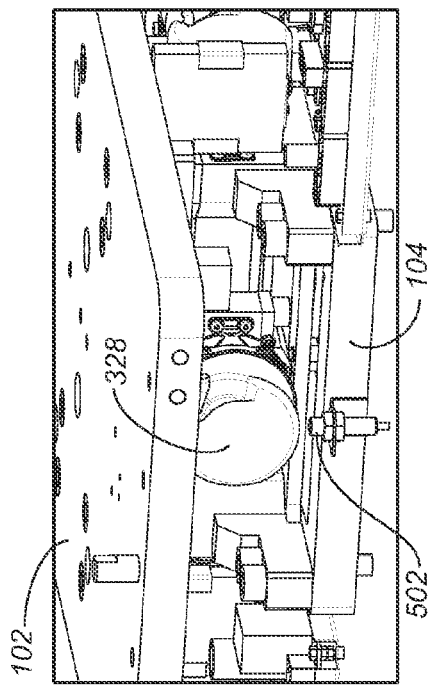
FIG. 5 shows an isometric view of a limit switch placed under an encoder in the couch top of FIG. 1 in one or more embodiments of the present disclosure.
Figure 6:
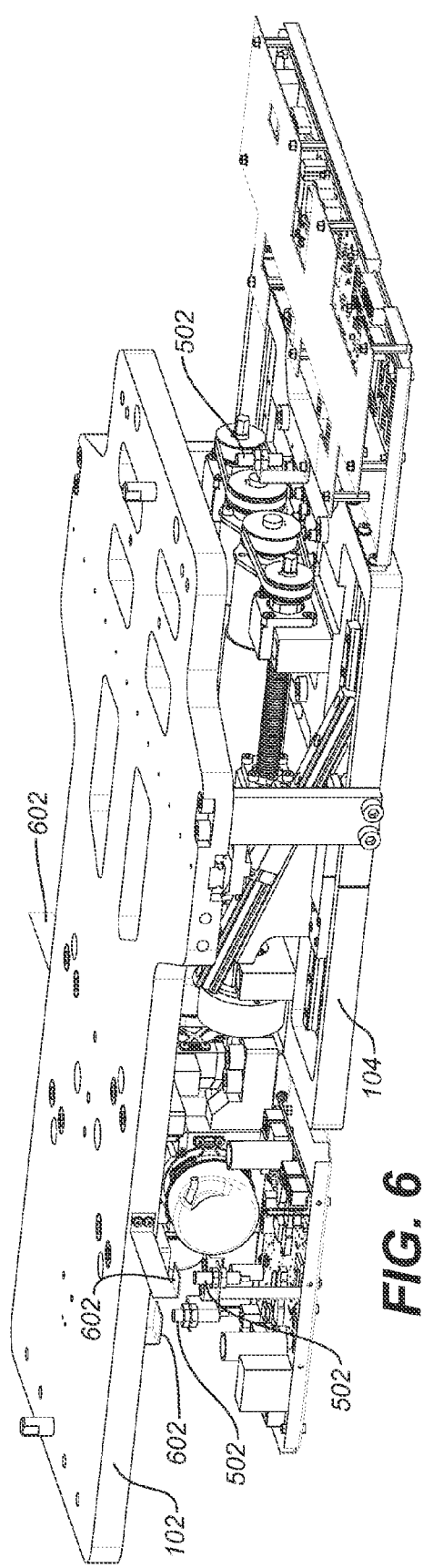
FIG. 6 shows an isometric view of limit switches placed under the back edge of the top plate and adjacent to the other sides of the top plate in the couch top of FIG. 1 in one or more embodiments of the present disclosure.

Positive and negative limit switches may be placed at positive and negative end pitch and roll positions. In one or more embodiments, a limit switch may be placed just under each encoder. For example, FIG. 5 shows a negative pitch limit switch 502 placed under encoder 328. In one or more embodiments, a limit switch 502 may be placed under or adjacent to each edges of top plate 102. For example, FIG. 6 shows a positive pitch limit switch 502 placed under the back edge of top plate 102. FIG. 6 also shows limit switches 502 placed adjacent to the other three sides of top plate 102 where extensions 602 may be used to trigger these limit switches 502.

In operation, motor 401 rotates spindle shaft 408. The rotation of spindle shaft 408 may translate wedge link 410 and wedge 412 along the Y direction. The translation of wedge 412 translates spherical bushing 428 up or down along the Z direction. The up or down motion of spherical bushing 428 pitches and/or rolls top plate 102 (FIG. 2A) along with any up or down motion from the other wedge actuator.

Wedge actuator 204 can be implemented in other manners. In some embodiments, screw drive 407 may be directly integrated with wedge assembly 412 instead of being arranged side-by-side and linked by wedge link 410. In some embodiments, screw drive 407 may be directly driven by motor 401 and gearbox 402 on spindle shaft 408 without pulleys and timing belt 406. In some embodiments, a servo controlled pneumatic cylinder with a linear feedback device may be used to translate wedge assembly 412 instead of motor 401, resolver 403, and screw drive 407.

Figure 7:
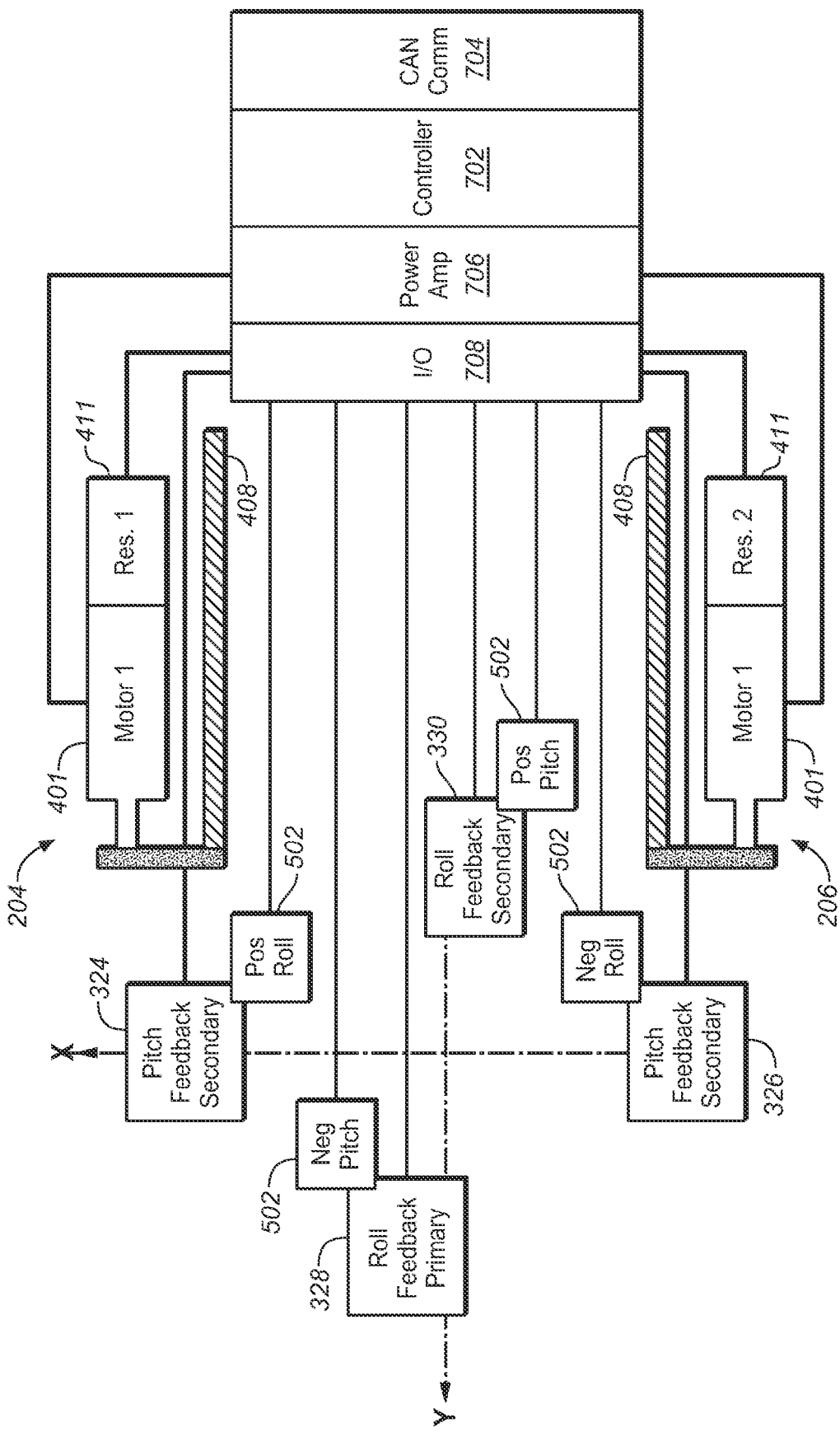
FIG. 7 illustrates a schematic of the couch top of FIG. 1 in one or more embodiments of the present disclosure.

FIG. 7 illustrates a schematic of couch top 100 in one or more embodiments of the present disclosure. Couch top 100 includes a controller 702 coupled to a communication interface 704, a power amplifier 706, and an input/output 708. Controller 702 uses communication interface 704 to receive and/or send orders and statuses. In one or more embodiments, controller 702 receives orders from and sends statuses to one or more external controllers that also control the motions of treatment couch 110. The orders may be any given or final pitch and roll angles to be translated into motor commands by controller 702, or the motor commands themselves. Controller 702 provides the motor commands to power amplifier 706, which in turn drives wedge actuators 204 and 206. Controller 702 may be connected to encoders 324, 326, 328, 330, resolvers 411, and limit switches 502 to receive feedbacks for a closed-control loop. Controller 702 uses the feedbacks from encoders 324, 326, 328, 330 and resolvers 411 to control the motion of top plate 102 (FIG. 2A). When triggered, limit switches 502 cause controller 702 to cut power to motors 401 and/or apply brakes 411 (FIG. 4A) to stop any motion. Limit switches 502 may be identified to controller 702 by their locations (e.g., positive pitch, negative pitch, positive roll, and negative roll). Controller 702 may send the feedbacks to the one or more external controllers when the one or more external controllers implement the closed-control loop and provides the motor commands.

Figure 8:
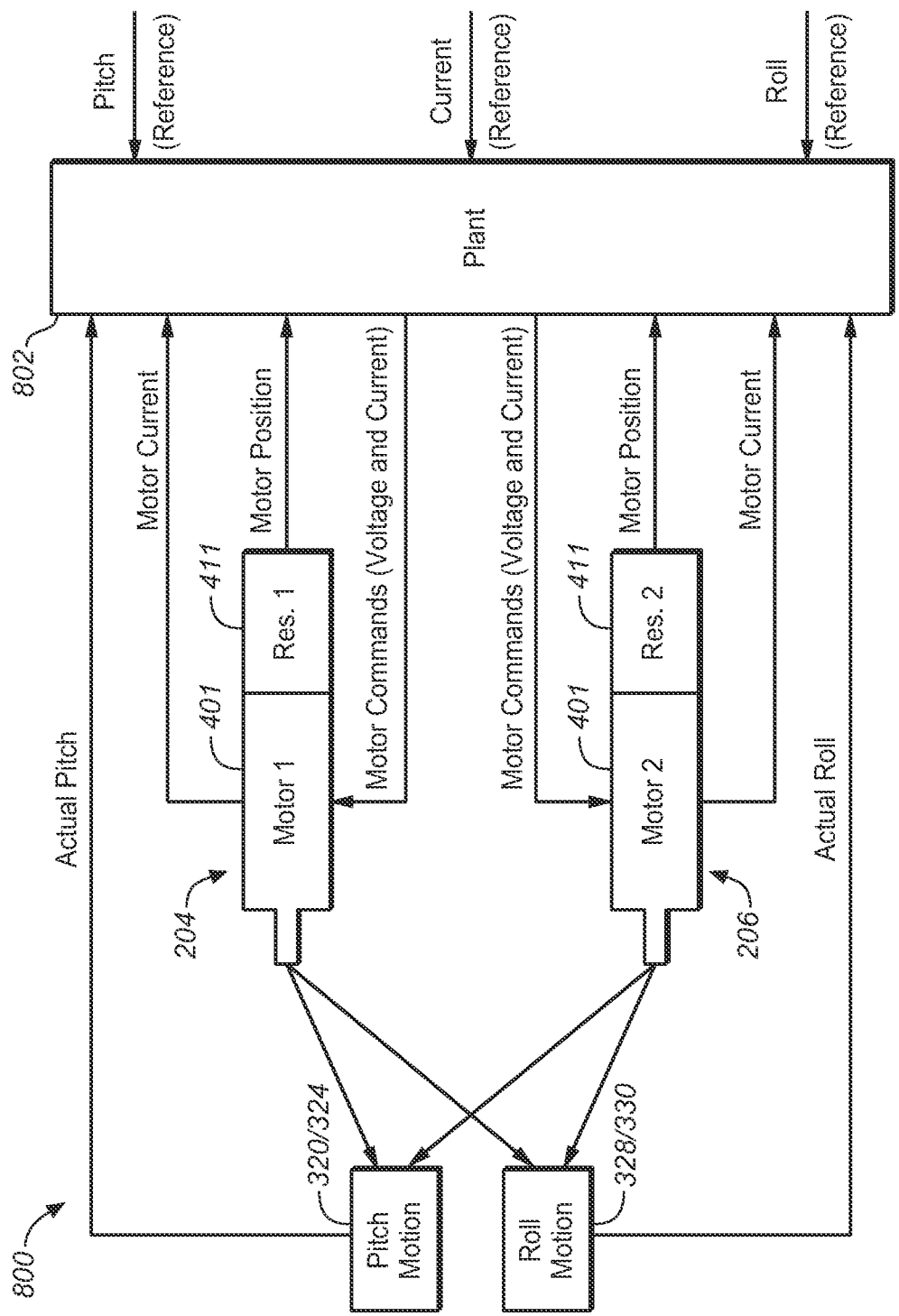
FIG. 8 illustrates a closed-control loop implemented by a controller for the couch top of FIG. 1 in one or more embodiments of the present disclosure.

FIG. 8 illustrates a closed-control loop 800 with a plant 802 implemented by controller 702 (FIG. 7) in one or more embodiments of the present disclosure. Controller 702, either alone or in combination with the one or more external controllers, receives reference (target) pitch and roll angles of top plate 102 (FIG. 2A) and compares them against actual pitch and roll angles measured by encoders 324, 326, 328, and 330. Based on their differences, controller 702 determines the reference (target) rotational positions of motors 401 in wedge actuators 204 and 206 to orient top plate 102 at the reference pitch and roll angles. Controller 702 compares the reference rotational positions of motors 401 against actual rotational positions of the motors measured by resolvers 411 in wedge actuators 204 and 206. Based on their differences, controller 702 determines the motor commands (e.g., voltages and currents) for driving motors 401 to the reference rotational positions. Controller 702 also compares feedback currents from motors 401 with a reference current to determine the necessary current to overcome background friction and load, and then adjusts the motor commands to achieve the desired end position. The pitch and the roll motion of top plate 102 may be detected by encoders 324, 326, 328, and 330 and fed back to controller 702.

Figure 9:
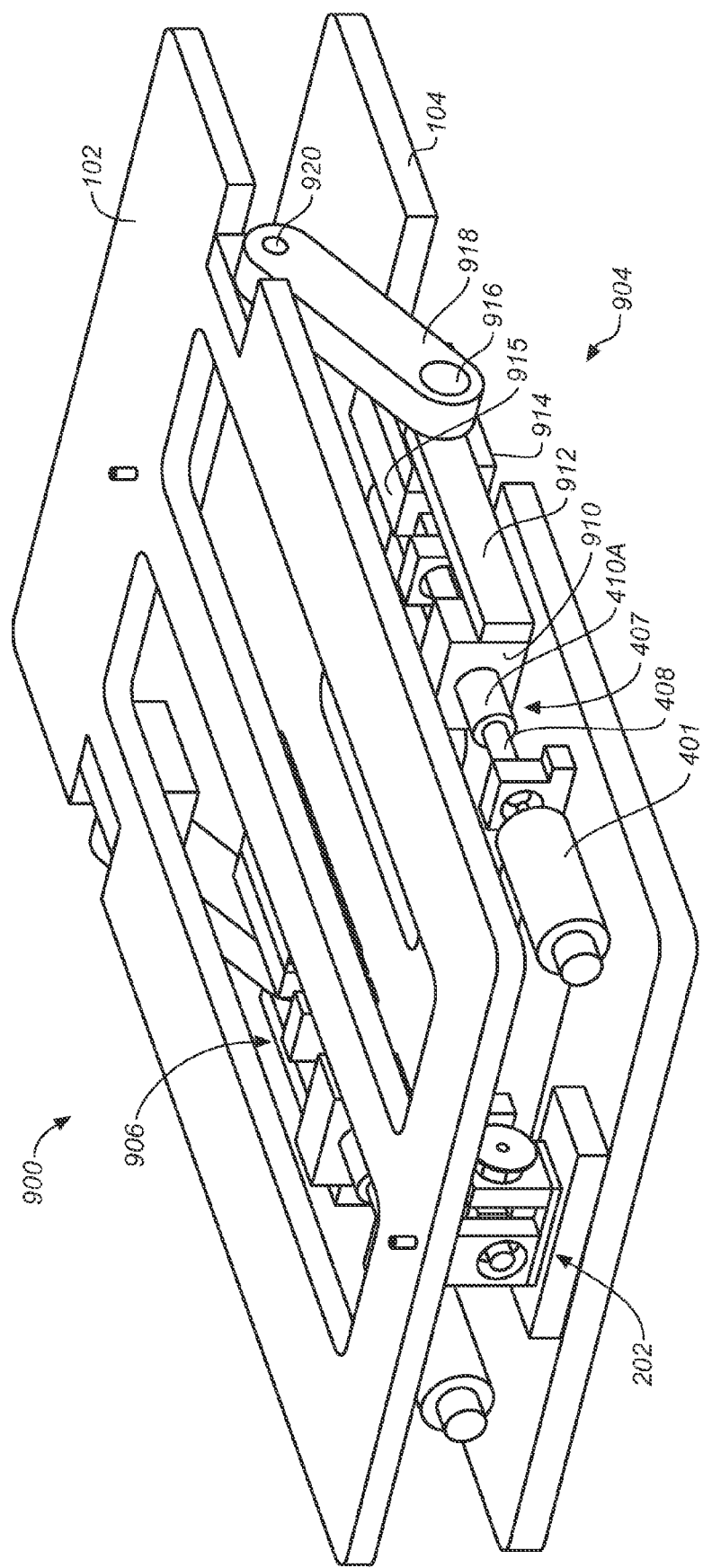
FIGS. 9 and 10 show isometric and side views of a couch top in one or more embodiments of the present disclosure.
Figure 10:
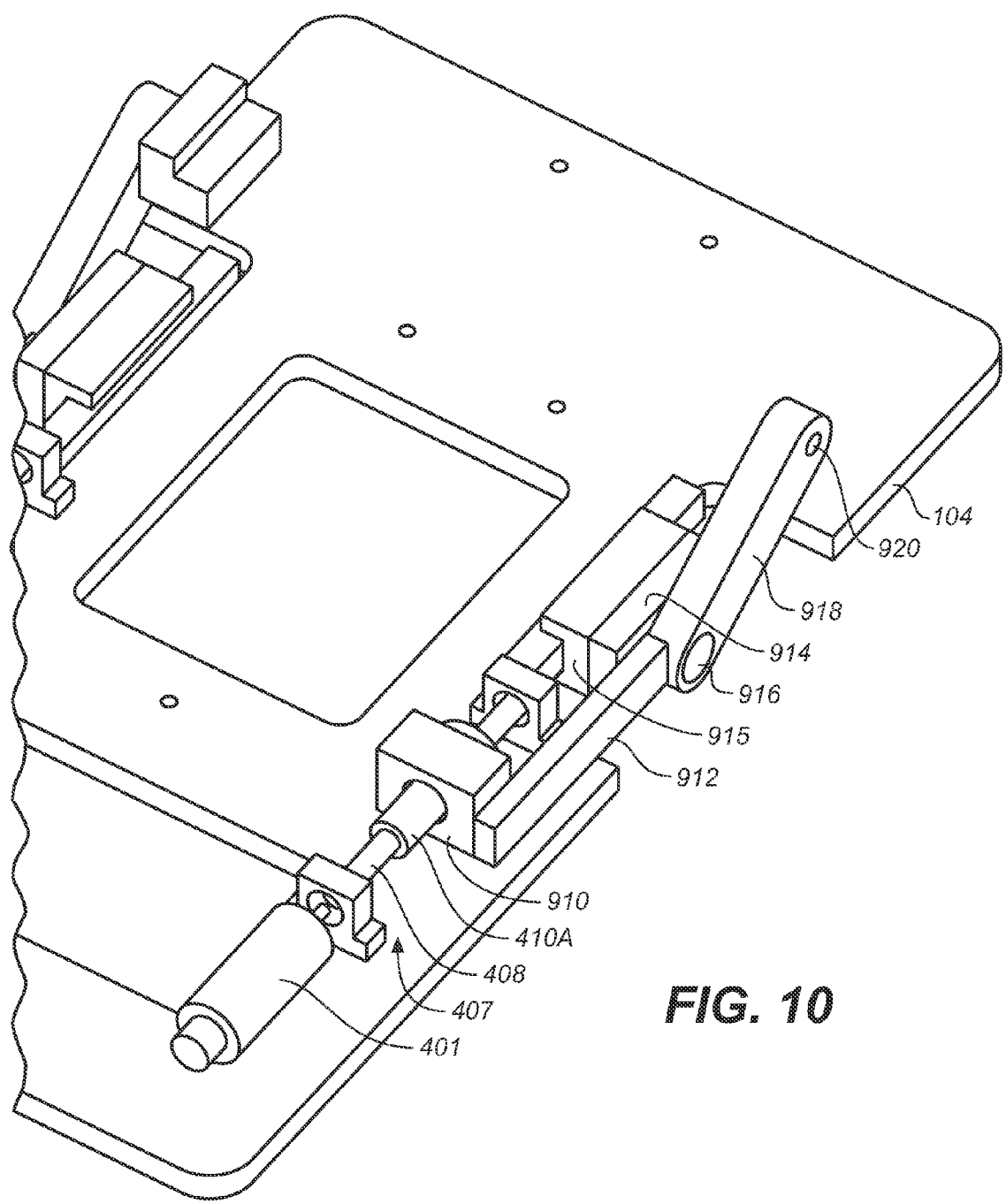

FIGS. 9 and 10 show isometric and side views of a couch top 900 in one or more embodiments of the present disclosure. Universal joint 202 may be located at the forward end of couch top 900 toward a radiation delivery apparatus. Universal joint 202 may be mounted on base plate 104 and connected to the bottom of top plate 102. Rotary feedback devices may be directly connected to the shafts of universal joint 202 to detect the pitch and the roll angles.

Top plate 102 may be actuated by two identical, symmetrically arranged bar-linkage actuators 904 and 906 on base plate 104. Actuators 904 and 906 may be located near the back end of couch top 900 away from the radiation delivery apparatus. Each actuator includes motor 401 driving screw drive 407. Screw drive 407 translates ball screw or nut 410A on spindle shaft 408. Ball screw or nut 410A may be fixed to a block 910, which may be fixed to a first link 912. First link 912 may be fixed to a block 914, which may be fixed to a traveler block 915 mounted on a linear rail. Block 914 may be coupled by an alignment needle bearing or spherical bushing 916 to a link 918. Link 918 may be coupled by an alignment needle bearing or spherical bushing 920 to top plate 102. So configured, the linear translation of link 912 along a horizontal direction causes a rotation of link 918 about bearing or bushing 916 so its distal end at bearing or bushing 920 raises or lowers top plate 102.

Various other adaptations and combinations of features of the embodiments disclosed are within the scope of the invention. As described above, couch top 100 may be used to position a patient for treatment. Couch top 100 may also be used to dynamically compensate the detected motion of a target, such as tumor movement from respiration. In addition to positioning a patient, couch top 100 may be adopted to manipulate other objects. For example, universal joint 202 and wedge actuators 204 may be adopted to manipulate a radiologic phantom to simulate tumor movement for treatment planning 2 DOF couch top 100 may also be used to correct imperfections in 4 DOF treatment couch 110. For example, treatment couch 110 may sag slightly when it extends laterally. The small sag results in a roll error that can be corrected with couch top 100. Numerous embodiments are encompassed by the following claims.

The invention claimed is:
1. An assembly, comprising:
a first structural element;
a second structural element;
a universal joint connected between a top surface of the first structural element and a bottom surface of the second structural element so the second structural element is rotatable about first and second horizontal axes relative to the first structural element;
a first actuator connected between the top surface of the first structural element and the bottom surface of the second structural element, the first actuator comprising a first actuated end that translates substantially parallel to a vertical axis, the first actuated end being coupled to vertically move the second structural element; and
a second actuator connected between the top surface of the first structural element and the bottom surface of the second structural element, the second actuator comprising a second actuated end that translates substantially parallel to the vertical axis, the second actuated end being coupled to vertically move the second structural element, wherein the first and the second actuators provide pitch and roll motions to the second structural element.

2. The assembly of claim 1, wherein each of the first and the second actuators comprises:
a wedge assembly to convert a horizontal translation to a vertical translation, comprising:
a first carriage on the top surface of the first structural element, the first carriage being translatable along a first horizontal direction, the first carriage comprising an inclined plane;
a second carriage on the inclined plane;
a third carriage translatable against the bottom surface of the second structural element, the third carriage being translatable along a second horizontal direction perpendicular to the first horizontal direction, the third carriage comprising a spherical bushing; and
a fastener securing the third carriage through the spherical bushing to the second carriage.

3. The assembly of claim 2, wherein the first horizontal direction is substantially parallel to the first horizontal axis and the second horizontal direction is substantially parallel to the second horizontal axis.

4. The assembly of claim 2, wherein:
the first carriage comprises one or more first linear bearings that engage one or more first rails mounted along the first horizontal direction on the first structural element;
the second carriage comprises one or more second linear bearings that engage one or more second rails mounted along the first horizontal direction on the inclined plane; and
the third carriage comprises one or more third linear bearings that engage one or more third rails mounted along the second horizontal direction on the bottom surface of the second structural element.

5. The assembly of claim 2, wherein each of the first and the second actuators comprises:
a screw drive to convert rotations to the horizontal translation, comprising:
a spindle shaft; and
a wedge link comprising or being attached to a nut on the spindle shaft, the wedge link being coupled to the first carriage; and
a motor coupled to the spindle shaft to provide the rotations.

6. The assembly of claim 5, further comprising brakes coupled to the spindle shafts of the first and the second actuators.

7. The assembly of claim 5, wherein the universal joint comprises a cross shaft with first and second shafts, the assembly further comprising:
a first rotary feedback device on one end of the first shaft;
a second rotary feedback device on one end of the second shaft; and
third and fourth rotary feedback devices coupled to the motors of the first and the second actuators.

8. The assembly of claim 7, wherein the first, the second, the third, and the fourth rotary feedback devices comprise absolute encoders, incremental encoders, resolvers, potentiometers, or Hall-effect sensors.

9. The assembly of claim 7, further comprising:
a communication interface;
a power amplifier coupled to the motors;
an input/output (I/O) interface coupled to the first, the second, the third, and the fourth rotary feedback devices; and
a controller coupled to the communication interface, the power amplifier, and the I/O interface.

10. The assembly of claim 9, wherein the controller is configured to:
receive, via the communication interface, a reference pitch about the first horizontal axis and a reference roll about the second horizontal axis;
receive, via the I/O interface, an actual pitch and an actual roll from the first and the second rotary feedback devices on the universal joint;
determine reference positions for the motors based on a difference between the reference and the actual pitches and a difference between the reference and the actual rolls;
receive, via the I/O interface, measured positions of the motors from the third and the fourth rotary feedback devices;
determine motor commands for the motors based on the differences between the reference and the measured positions of the motors; and
instruct the power amplifier with the motor commands for the motors.

11. The assembly of claim 10, wherein the controller is further configured to adjust the motor commands based on differences between feedback currents and a reference current.

12. The assembly of claim 9, wherein the controller is configured to:
receive, via the communication interface, motor commands from an other controller;
provide the motor commands to the power amplifier;
receive, via the I/O interface, a measured pitch and a measured roll from the first and the second rotary feedback devices on the universal joint;
receive, via the I/O interface, measured positions of the motors from the third and the fourth rotary feedback devices; and
send, via the communication interface, the measured pitch, the measured roll, and the measured positions of the motors to the other controller.

13. The assembly of claim 2, wherein each of the first and the second actuators comprises a servo controlled pneumatic cylinder driving the first carriage.

14. The assembly of claim 2, wherein the universal joint comprises a cross shaft with first and second shafts, the assembly further comprising:
first and second rotary feedback devices on ends of the first shaft; and
third and fourth rotary feedback devices on ends of the second shaft.

15. The assembly of claim 14, further comprising limit switches mounted on the first structural element at locations below the first, the second, the third, and the fourth rotary feedback devices, the limit switches being configured to be triggered by movements of the first, the second, the third, and the fourth rotary feedback devices.

16. The assembly of claim 1, further comprising limit switches mounted on the first structural element at locations at or proximate to edges of the second structural element, the limit switches being configured to be triggered by the edges or extenders from the edges.

17. The assembly of claim 1, wherein the universal joint further comprises:
a cross shaft comprising first and second shafts;
an upper mount comprising first bearing housings;

first bearings being mounted to the ends of the second shaft, the first bearings seated in the first bearing housings;

a lower mount comprising second bearing housings; and second bearings mounted to the ends of the first shaft, the second bearings seated in the second bearing housings.

18. The assembly of claim 17, wherein the universal joint further comprises:

first adjustable hard stops extending from the upper mount toward the second shaft to limit rotation of the first shaft; and second adjustable hard stops extending from the lower mount toward the first shaft to limit rotation of the second shaft.

19. The assembly of claim 1, wherein each of the first and the second actuators comprises:

a first link being translatable along a first horizontal direction on the first structural element; and a second link having a first end coupled to the first link and a second end coupled to the second structural element.

20. The assembly of claim 1, wherein the first structural element is a base plate or frame, and the second structural element is a top plate or frame.

21. The assembly of claim 1, wherein each of the first and the second actuators is a wedge actuator comprising a motor, a screw drive that converts multiple rotations of the motor into a horizontal displacement, and a wedge assembly that converts the horizontal displacement of the screw drive into a vertical displacement smaller than the horizontal displacement.

22. A couch top for positioning a patient, comprising:
a base, comprising;
  a top side; and
  one or more first rails mounted on the top side parallel to a Y axis;
a top, comprising:
  a bottom side; and
  one or more second rails mounted to the bottom side parallel to an X axis
a universal joint coupled between the top and the base so the top is rotatable about the X and the Y axes, the universal joint comprising a cross shaft with a pitch shaft and a roll shaft;
a first primary encoder on one end of the pitch shaft;
a first secondary encoder on another end of the pitch shaft;
a second primary encoder on one end of the roll shaft;
a second secondary encoder on another end of the roll shaft;

first and second actuators mounted on the base, the first and the second actuators being coupled to the top on different sides of the Y axis, each of the first and the second actuators comprising:
  a motor;
  a resolver on the motor;
  a screw drive, comprising:
    a spindle shaft coupled to the motor; and
    a wedge link comprising or being attached to a nut on the spindle shaft;
  a wedge assembly, comprising:
    a first carriage coupled to the wedge link, the first carriage comprising one or more first linear bearings riding on the one or more first rails on the base, the first carriage comprising one or more inclined rails parallel to the Y axis;
    a second carriage comprising one or more second linear bearings riding on the one or more inclined rails;
    a third carriage comprising one or more third linear bearings engaging the one or more second rails on the bottom side of the top, the third carriage comprising a spherical bushing; and
    a fastener securing the third carriage through the spherical bushing to the second carriage;
a communication interface;
a power amplifier coupled to motors of the first and the second actuators;
an input/output (I/O) interface coupled to the first, the second, the third, and the fourth encoders and the resolvers; and
a controller coupled to the communication interface, the power amplifier, and the I/O interface.

23. An assembly, comprising:
a first structural element;
a second structural element;
a joint means coupled between the first structural element and the second structural element so one structural element is rotatable about first and second horizontal axes relative to the other structural element; and
first and second actuating means coupled between the first and the second structural elements, wherein each of the first and the second actuating means provides precise control by converting multiple rotations to a horizontal displacement and the horizontal displacement to a vertical displacement smaller than the horizontal displacement.

* * * * *